(12) United States Patent
O'Brien et al.

(10) Patent No.: US 12,171,954 B2
(45) Date of Patent: Dec. 24, 2024

(54) CAPS FOR CATHETER PACKAGES

(71) Applicant: Hollister Incorporated, Libertyville, IL (US)

(72) Inventors: Daniel E. O'Brien, Calry (IE); Vincent Naughton, Sligo (IE); Martin P. Creaven, Ballina (IE); Scott J. Pupino, Lakewood, IL (US); Daniel A. March, Lake Villa, IL (US); Joseph N. Hanley, Sligo (IE); Kevin Anthony Ludlow, Drumsna (IE); Paige Erin Kendell, Pittsburgh, PA (US); Jeffrey A. Ambourn, Eau Claire, WI (US); David Benjamin Wolgemuth, Elk Mound, WI (US); David Louis Nett, Hudson, WI (US); Brandon Lee Michal, Chippewa Falls, WI (US); Christopher L. Belisle, Somerset, WI (US); Timothy Alan Parmer, Saint Paul, MN (US)

(73) Assignee: Hollister Incorporated, Libertyville, IL (US)

( * ) Notice: Subject to any disclaimer, the term of this patent is extended or adjusted under 35 U.S.C. 154(b) by 0 days.

(21) Appl. No.: 18/458,421

(22) Filed: Aug. 30, 2023

(65) Prior Publication Data

US 2023/0405267 A1   Dec. 21, 2023

Related U.S. Application Data

(62) Division of application No. 18/074,794, filed on Dec. 5, 2022, now Pat. No. 11,771,865, which is a division
(Continued)

(51) Int. Cl.
*A61M 25/00* (2006.01)
*B65D 43/16* (2006.01)
(Continued)

(52) U.S. Cl.
CPC ......... *A61M 25/002* (2013.01); *B65D 43/162* (2013.01); *B65D 43/22* (2013.01);
(Continued)

(58) Field of Classification Search
CPC ............ A61M 25/002; A61M 25/0017; A61M 25/01; A61M 25/0111; A61M 25/0113;
(Continued)

(56) References Cited

U.S. PATENT DOCUMENTS

| 2,040,798 A | 5/1936 | Schoonmaker |
| 2,445,395 A | 7/1948 | Greene et al. |

(Continued)

FOREIGN PATENT DOCUMENTS

| AT | 369994 B | 2/1983 |
| CN | 2078634 U | 6/1991 |

(Continued)

OTHER PUBLICATIONS

International Search Report and Written Opinion, issued in connection with International Application No. PCT/US2017/028979 on Aug. 25, 2017.

(Continued)

*Primary Examiner* — Chun Hoi Cheung
*Assistant Examiner* — Brijesh V. Patel
(74) *Attorney, Agent, or Firm* — Cook Alex Ltd.

(57) ABSTRACT

A urinary catheter package with a case having a hollow tube which is closed at one end and open at the other end, the hollow tube having a wall and a pierceable cover attached to the open end of the hollow tube. Also an assembly including the urinary catheter package and a catheter with a funnel at a first end.

20 Claims, 6 Drawing Sheets

Related U.S. Application Data of application No. 16/755,310, filed as application No. PCT/US2018/056693 on Oct. 19, 2018, now abandoned.

(60) Provisional application No. 62/577,035, filed on Oct. 25, 2017.

(51) Int. Cl.
*B65D 43/22* (2006.01)
*B65D 43/24* (2006.01)
*B65D 53/02* (2006.01)

(52) U.S. Cl.
CPC .............. *B65D 43/24* (2013.01); *B65D 53/02* (2013.01); *B65D 2543/00092* (2013.01); *B65D 2543/00231* (2013.01); *B65D 2543/00296* (2013.01); *B65D 2543/00351* (2013.01); *B65D 2543/00527* (2013.01); *B65D 2543/00546* (2013.01); *B65D 2543/00564* (2013.01); *B65D 2543/00842* (2013.01)

(58) Field of Classification Search
CPC .......... A61M 25/0045; A61M 25/0097; A61M 2025/0046; A61M 2025/586; A61M 2025/0062; A61M 27/00; A61M 5/002; A61M 5/5086; A61M 2039/1033; A61M 2209/06; A61M 2210/1085; A61M 39/162; A61M 39/20; B65D 43/162; B65D 47/0838; B65D 47/141; B65D 50/045; B65D 55/16; B65D 2251/1025; B65D 2251/1016; B65D 2251/20; B65D 2215/02; B65D 2543/00296; B65D 2543/00842; A61J 1/03; A61J 1/1425; A61J 1/065; A61J 1/1412; A61J 1/1481; A61J 1/1487; A61J 1/2048; A61J 1/2065; A61J 1/2096
USPC ........ 215/237, 216–218, 211, 235, 245, 206, 215/209, 213, 24, 250, 253, 277–278, 215/306, 308, 317, 354, 382, DIG. 3; 206/363–364, 438–439, 210, 305, 361, 206/365, 370, 443, 45.24, 480, 484.1, 206/807, 0.5; 220/324, 254.1, 254.3, 220/254.5, 258.1, 258.3, 259.1–259.3, 220/315, 367.1, 810, 834–835, 847, 268, 220/283, 292, 326, 360, 371, 375, 378, 220/529, 560.01, 833, 837, 839; 222/556, 222/153.14, 153.01, 153.05–153.07, 543, 222/566; 604/544, 263–264
See application file for complete search history.

(56) References Cited

U.S. PATENT DOCUMENTS

| | | | |
|---|---|---|---|
| 2,582,489 A | 1/1952 | Krueger | |
| 2,991,913 A | 7/1961 | Goth | |
| 3,114,455 A | 12/1963 | Claisee et al. | |
| 3,149,717 A * | 9/1964 | Castelli | A61M 5/3202 206/459.1 |
| 3,203,545 A | 8/1965 | Grossman | |
| 3,369,542 A | 2/1968 | Thaidigsman | |
| 3,794,042 A | 2/1974 | De Klotz et al. | |
| 3,854,483 A | 12/1974 | Powers | |
| 3,867,945 A | 2/1975 | Long | |
| 3,894,540 A | 7/1975 | Bonner | |
| 3,920,023 A | 11/1975 | Dye | |
| 3,934,722 A * | 1/1976 | Goldberg | B65D 41/32 215/253 |
| 4,043,345 A | 8/1977 | Kramann et al. | |
| 4,061,226 A * | 12/1977 | Essen | G01K 13/25 220/259.2 |
| 4,109,659 A | 8/1978 | Sheridan | |
| 4,113,090 A | 9/1978 | Carstens | |
| 4,248,214 A | 2/1981 | Hannah | |
| 4,553,959 A | 11/1985 | Hickey et al. | |
| D284,400 S * | 6/1986 | Wada | D3/203.1 |
| 4,684,369 A | 8/1987 | Wildemeersch | |
| 4,765,498 A | 8/1988 | Rafferty | |
| 4,773,901 A | 9/1988 | Norton | |
| 4,921,096 A | 5/1990 | McFarlane | |
| 4,935,017 A | 6/1990 | Sylvanowicz | |
| 4,956,298 A | 9/1990 | Diekmann | |
| 5,012,940 A | 5/1991 | Koehn | |
| D320,694 S * | 10/1991 | Brant | D3/260 |
| 5,084,036 A | 1/1992 | Rosenbaum | |
| 5,149,326 A | 9/1992 | Woodgrift et al. | |
| 5,217,114 A | 6/1993 | Gadberry et al. | |
| 5,225,165 A | 7/1993 | Perlman | |
| 5,240,131 A | 8/1993 | Keller | |
| 5,242,069 A | 9/1993 | Hertrampf | |
| 5,380,270 A | 1/1995 | Ahmadzadeh | |
| 5,413,561 A | 5/1995 | Fischell et al. | |
| 5,417,326 A | 5/1995 | Winer | |
| 5,519,931 A * | 5/1996 | Reich | G21F 5/018 588/259 |
| 5,582,314 A | 12/1996 | Quinn et al. | |
| 5,582,599 A | 12/1996 | Daneshvar | |
| 5,868,265 A | 2/1999 | Kobayashi | |
| 5,881,774 A | 3/1999 | Utterberg | |
| 5,919,170 A | 7/1999 | Woessner | |
| 5,960,972 A | 10/1999 | Larguia, Sr. | |
| 6,258,078 B1 | 7/2001 | Thilly | |
| 6,328,355 B1 | 12/2001 | Bortz | |
| 6,341,721 B1 | 1/2002 | Herald et al. | |
| 6,439,410 B1 | 8/2002 | Dubach | |
| 6,460,712 B2 | 10/2002 | Smith | |
| 6,460,726 B1 | 10/2002 | Hierzer et al. | |
| 6,576,918 B1 * | 6/2003 | Fu | G21F 5/018 206/524.1 |
| 6,585,721 B2 | 7/2003 | Fiore | |
| 6,634,498 B2 | 10/2003 | Kayerod et al. | |
| D488,864 S * | 4/2004 | Fago | D24/121 |
| 6,726,649 B2 | 4/2004 | Swenson et al. | |
| 6,822,253 B1 | 11/2004 | Martin et al. | |
| 6,871,753 B2 | 3/2005 | McHutchinson | |
| 6,908,013 B2 | 6/2005 | Thomson et al. | |
| 6,908,113 B2 | 6/2005 | Chaduc et al. | |
| 6,926,708 B1 | 8/2005 | Franks-Farah et al. | |
| 7,094,220 B2 * | 8/2006 | Tanghoj | B29C 45/16 604/528 |
| 7,120,487 B2 | 10/2006 | Nelson | |
| 7,306,128 B2 | 12/2007 | Eimer | |
| 7,311,698 B2 | 12/2007 | Tanghoj et al. | |
| 7,353,969 B2 | 4/2008 | McHutchinson | |
| 7,392,903 B2 * | 7/2008 | Jolley | A61B 50/362 206/363 |
| 7,438,704 B1 | 10/2008 | Kawashima et al. | |
| 7,546,931 B2 | 6/2009 | Giusti | |
| 7,571,804 B2 | 8/2009 | Kjellmann Bruun et al. | |
| 7,614,514 B2 | 11/2009 | Fuchs | |
| 7,699,168 B2 | 4/2010 | Ryan et al. | |
| 7,717,284 B2 | 5/2010 | Giusti | |
| 7,748,550 B2 | 7/2010 | Cho | |
| 7,867,220 B2 | 1/2011 | Tanghoj | |
| 7,886,907 B2 | 2/2011 | Murray et al. | |
| 7,967,744 B2 | 6/2011 | Kaye et al. | |
| 7,992,737 B2 | 8/2011 | Salice | |
| 8,137,309 B2 | 3/2012 | Nishtala et al. | |
| 8,172,101 B2 | 5/2012 | Giusti | |
| 8,181,778 B1 | 5/2012 | van Groningen et al. | |
| 8,230,993 B2 | 7/2012 | Tanghoej | |
| 8,361,057 B2 | 1/2013 | Tanghoej et al. | |
| 8,381,925 B2 | 2/2013 | Skillin et al. | |
| 8,398,615 B2 | 3/2013 | Torstensen et al. | |
| 8,434,639 B2 | 5/2013 | Markert | |
| 8,439,213 B2 | 5/2013 | Goria et al. | |
| 8,448,798 B2 | 5/2013 | Groubert et al. | |
| 8,491,568 B2 | 7/2013 | Schertiger et al. | |

(56) References Cited

U.S. PATENT DOCUMENTS

| | | | |
|---|---|---|---|
| 8,511,472 B2 | 8/2013 | Dupuis et al. | |
| 8,523,843 B2 | 9/2013 | Kavanagh et al. | |
| 8,529,549 B2 | 9/2013 | Tanghoj | |
| 8,579,115 B2 | 11/2013 | Murphy | |
| 8,616,406 B1 | 12/2013 | Sawicki | |
| 8,616,407 B2 | 12/2013 | Sawicki | |
| 8,733,566 B2 | 5/2014 | Druitt et al. | |
| 8,752,722 B2 | 6/2014 | Kuhn et al. | |
| 8,833,556 B2 * | 9/2014 | Wright | A61M 1/84 206/363 |
| 8,863,968 B2 | 10/2014 | Giusti | |
| 9,033,149 B2 | 5/2015 | Terry | |
| 9,090,386 B2 | 7/2015 | van Alfen et al. | |
| 9,220,866 B2 | 12/2015 | Skillin et al. | |
| 9,334,097 B2 | 5/2016 | Skillin et al. | |
| 9,352,318 B2 | 5/2016 | Giusti | |
| 9,415,909 B2 | 8/2016 | Druitt et al. | |
| 9,422,089 B2 | 8/2016 | Wheeler | |
| 9,501,958 B2 | 11/2016 | Pietarinen et al. | |
| 9,511,906 B2 | 12/2016 | van Alfen et al. | |
| 9,669,187 B2 | 6/2017 | Tjassens et al. | |
| 9,687,629 B1 | 6/2017 | Palmer | |
| 9,701,451 B2 | 7/2017 | Skillin et al. | |
| 10,857,068 B2 | 12/2020 | Davis et al. | |
| 2001/0001443 A1 | 5/2001 | Kayerod et al. | |
| 2001/0037954 A1 | 11/2001 | Schmidt et al. | |
| 2003/0004496 A1 * | 1/2003 | Tanghoj | A61M 25/0017 604/544 |
| 2003/0060807 A1 | 3/2003 | Tanghoj | |
| 2003/0141210 A1 | 7/2003 | Yanke et al. | |
| 2004/0016714 A1 | 1/2004 | Wood | |
| 2004/0150221 A1 | 8/2004 | Brown | |
| 2005/0067366 A1 | 3/2005 | Dubach | |
| 2005/0080430 A1 * | 4/2005 | Wright, Jr. | A61B 17/3468 606/108 |
| 2005/0106339 A1 | 5/2005 | Baker | |
| 2005/0106340 A1 | 5/2005 | Baker | |
| 2005/0274687 A1 | 12/2005 | McCutchan | |
| 2006/0091670 A1 | 5/2006 | Gaynor | |
| 2006/0116661 A1 | 6/2006 | Tanghoej | |
| 2006/0142737 A1 | 6/2006 | Tanghoj | |
| 2006/0180585 A1 | 8/2006 | Cunningham et al. | |
| 2007/0034537 A1 | 2/2007 | Fago et al. | |
| 2007/0068977 A1 | 3/2007 | Voget et al. | |
| 2008/0183181 A1 | 7/2008 | Treacy et al. | |
| 2008/0260576 A1 * | 10/2008 | Bruun | A61M 25/0111 206/364 |
| 2008/0264961 A1 | 10/2008 | Sawyer | |
| 2008/0319423 A1 | 12/2008 | Tanghoj et al. | |
| 2009/0008279 A1 | 1/2009 | Tanghoej | |
| 2009/0050253 A1 | 2/2009 | Thomas et al. | |
| 2009/0054876 A1 | 2/2009 | Borodulin | |
| 2009/0299334 A1 | 12/2009 | Nishtala et al. | |
| 2010/0106236 A1 | 4/2010 | Nelson | |
| 2010/0211050 A1 | 8/2010 | Luther | |
| 2010/0224643 A1 | 9/2010 | Daggett | |
| 2010/0256580 A1 | 10/2010 | Faber | |
| 2010/0324540 A1 | 12/2010 | Paulen et al. | |
| 2011/0060317 A1 | 3/2011 | Fröjd | |
| 2011/0224653 A1 | 9/2011 | Torstensen | |
| 2012/0016318 A1 | 1/2012 | Hoang et al. | |
| 2012/0051967 A1 | 3/2012 | Murphy et al. | |
| 2012/0165791 A1 | 6/2012 | Lovmar et al. | |
| 2012/0179144 A1 | 7/2012 | Carleo | |
| 2012/0271281 A1 | 10/2012 | Schertiger | |
| 2013/0068767 A1 | 3/2013 | Fraser et al. | |
| 2013/0134123 A1 | 5/2013 | Fraser et al. | |
| 2013/0150828 A1 | 6/2013 | Conway | |
| 2013/0161344 A1 | 6/2013 | Park et al. | |
| 2013/0186791 A1 | 7/2013 | Triquigneaux | |
| 2013/0218136 A1 | 8/2013 | Tanghoej et al. | |
| 2013/0240393 A1 | 9/2013 | Bode et al. | |
| 2013/0289537 A1 | 10/2013 | Schertiger | |
| 2013/0299516 A1 | 11/2013 | Dupuis et al. | |
| 2013/0327664 A1 | 12/2013 | Tanghoj | |
| 2014/0162860 A1 | 9/2014 | Hagel | |
| 2014/0262860 A1 | 9/2014 | Mitten et al. | |
| 2014/0263436 A1 | 9/2014 | Gelov et al. | |
| 2014/0360896 A1 | 12/2014 | Torstensen | |
| 2016/0016703 A1 | 1/2016 | Mühlemann | |
| 2016/0023816 A1 | 1/2016 | Giraud | |
| 2016/0023818 A1 | 1/2016 | Gelov et al. | |
| 2016/0059999 A1 | 3/2016 | Forster | |
| 2016/0193447 A1 | 7/2016 | Matthiassen | |
| 2016/0325895 A1 | 11/2016 | Browning | |
| 2016/0332789 A1 | 11/2016 | Yerecic | |
| 2017/0014597 A1 | 1/2017 | Hagel | |
| 2017/0080177 A1 | 3/2017 | Tanghoej et al. | |
| 2017/0107365 A1 | 4/2017 | Rycroft et al. | |
| 2017/0166369 A1 | 6/2017 | Mitten et al. | |
| 2017/0173300 A1 | 6/2017 | Hannon et al. | |
| 2017/0175428 A1 | 6/2017 | Quinn et al. | |
| 2017/0326334 A1 | 11/2017 | Terry | |

FOREIGN PATENT DOCUMENTS

| | | |
|---|---|---|
| DE | 20117438 U1 | 3/2002 |
| DE | 10213411 A1 | 10/2003 |
| DE | 20317135 U1 | 1/2004 |
| DE | 202005008071 U1 | 7/2005 |
| DE | 102004013712 B3 | 8/2005 |
| DE | 202005009946 U1 | 9/2005 |
| DE | 202006013663 U1 | 11/2006 |
| DE | 202010006267 U1 | 11/2010 |
| DE | 202010007433 U1 | 6/2011 |
| DE | 202011107025 U1 | 1/2013 |
| DE | 202011107059 U1 | 1/2013 |
| DE | 102013014483 A1 | 6/2014 |
| DE | 202017101126 U1 | 4/2017 |
| DE | 102016205834 | 5/2017 |
| DK | 173714 B1 | 7/2001 |
| EP | 0041487 A1 | 12/1981 |
| EP | 0134630 A1 | 3/1985 |
| EP | 0781572 A2 | 7/1997 |
| EP | 0812287 A1 | 12/1997 |
| EP | 0861639 A2 | 9/1998 |
| EP | 0910425 A1 | 4/1999 |
| EP | 0923398 A1 | 6/1999 |
| EP | 0933304 A1 | 8/1999 |
| EP | 1023882 A1 | 2/2000 |
| EP | 0996542 A1 | 5/2000 |
| EP | 1086024 A1 | 3/2001 |
| EP | 1334039 A1 | 8/2003 |
| EP | 1392575 A1 | 3/2004 |
| EP | 1409369 A1 | 4/2004 |
| EP | 1466645 A2 | 10/2004 |
| EP | 1487712 A2 | 12/2004 |
| EP | 1593710 A1 | 11/2005 |
| EP | 1615960 A1 | 1/2006 |
| EP | 1634554 A2 | 3/2006 |
| EP | 1638856 A1 | 3/2006 |
| EP | 1317382 A1 | 6/2006 |
| EP | 1671663 A1 | 6/2006 |
| EP | 1696990 A1 | 9/2006 |
| EP | 1720772 A1 | 11/2006 |
| EP | 1278679 A1 | 6/2007 |
| EP | 1858575 A1 | 11/2007 |
| EP | 1863719 A2 | 12/2007 |
| EP | 1799574 B1 | 1/2008 |
| EP | 1878461 A1 | 1/2008 |
| EP | 1897579 A1 | 3/2008 |
| EP | 1897580 A1 | 3/2008 |
| EP | 1963195 A2 | 9/2008 |
| EP | 1966058 A1 | 9/2008 |
| EP | 1979032 A1 | 10/2008 |
| EP | 1982741 A2 | 10/2008 |
| EP | 1986921 A1 | 11/2008 |
| EP | 2035292 A2 | 3/2009 |
| EP | 2042211 A1 | 4/2009 |
| EP | 2044963 A1 | 4/2009 |
| EP | 2060296 A1 | 5/2009 |
| EP | 2072075 A1 | 6/2009 |
| EP | 2106821 A1 | 10/2009 |
| EP | 2242696 A1 | 10/2010 |

(56) References Cited

FOREIGN PATENT DOCUMENTS

| | | |
|---|---|---|
| EP | 2250102 A1 | 11/2010 |
| EP | 2251454 A2 | 11/2010 |
| EP | 2292294 A1 | 3/2011 |
| EP | 2308543 A1 | 4/2011 |
| EP | 2295108 A1 | 6/2011 |
| EP | 2450076 A1 | 5/2012 |
| EP | 2468319 A1 | 6/2012 |
| EP | 2325100 B1 | 8/2012 |
| EP | 2504054 A1 | 10/2012 |
| EP | 2515985 A1 | 10/2012 |
| EP | 2576374 A1 | 4/2013 |
| EP | 2596831 A2 | 5/2013 |
| EP | 2617316 A2 | 7/2013 |
| EP | 2638927 A2 | 9/2013 |
| EP | 2682069 A1 | 1/2014 |
| EP | 2686054 A1 | 1/2014 |
| EP | 2750748 A1 | 7/2014 |
| EP | 2774648 A1 | 9/2014 |
| EP | 2782842 A1 | 10/2014 |
| EP | 2785409 A1 | 10/2014 |
| EP | 2823845 A1 | 1/2015 |
| EP | 3033279 A1 | 6/2016 |
| EP | 3038075 A2 | 6/2016 |
| EP | 3113922 A1 | 1/2017 |
| EP | 2605977 B1 | 5/2017 |
| EP | 3210909 A1 | 8/2017 |
| EP | 3298620 A1 | 3/2018 |
| FR | 2717676 A1 | 9/1995 |
| GB | 2031735 A | 4/1980 |
| GB | 2033231 A | 5/1980 |
| GB | 2322079 A | 8/1998 |
| JP | 2011025473 A | 2/2011 |
| KR | 20110101674 A | 9/2011 |
| PT | 2216064 T | 9/2016 |
| SE | 514121 C2 | 1/2001 |
| WO | WO 96/08219 A1 | 3/1996 |
| WO | WO 97/26937 A1 | 7/1997 |
| WO | WO 97/41811 A1 | 11/1997 |
| WO | WO 98/11932 A1 | 3/1998 |
| WO | WO 98/19729 A1 | 5/1998 |
| WO | WO 99/30761 A1 | 6/1999 |
| WO | WO 99/42155 A2 | 8/1999 |
| WO | WO 00/16843 A1 | 3/2000 |
| WO | WO 00/30575 A1 | 6/2000 |
| WO | WO 00/47494 A1 | 8/2000 |
| WO | WO 01/43807 A1 | 6/2001 |
| WO | WO 01/60255 A1 | 8/2001 |
| WO | WO 02/060361 A2 | 8/2002 |
| WO | WO 02/080843 A2 | 10/2002 |
| WO | WO 03/001994 A1 | 1/2003 |
| WO | WO 03/008028 A2 | 1/2003 |
| WO | WO 03/008029 A2 | 1/2003 |
| WO | WO 03/022561 A1 | 3/2003 |
| WO | WO 03/045487 A2 | 6/2003 |
| WO | WO 03/061732 A2 | 7/2003 |
| WO | WO 03/092779 A1 | 11/2003 |
| WO | WO 03/097237 A2 | 11/2003 |
| WO | WO 2004/021890 A1 | 3/2004 |
| WO | WO 2004/035123 A1 | 4/2004 |
| WO | WO 2004032750 A1 | 4/2004 |
| WO | WO 2004/050155 A1 | 6/2004 |
| WO | WO 2004/054446 A1 | 7/2004 |
| WO | WO 2004/054653 A1 | 7/2004 |
| WO | WO 2004/056414 A1 | 7/2004 |
| WO | WO 2004/089454 A1 | 10/2004 |
| WO | WO 2004/103153 A2 | 12/2004 |
| WO | WO 2005/014055 A2 | 2/2005 |
| WO | WO 2005/092418 A1 | 10/2005 |
| WO | WO 2006/005349 A2 | 1/2006 |
| WO | WO 2006/017439 A2 | 2/2006 |
| WO | WO 2006/044249 A2 | 4/2006 |
| WO | WO 2006/044621 A2 | 4/2006 |
| WO | WO 2006/045809 A1 | 5/2006 |
| WO | WO 2006092150 A1 | 9/2006 |
| WO | WO 2006/121183 A1 | 11/2006 |
| WO | WO 2007/005851 A2 | 1/2007 |
| WO | WO 2007/022223 A2 | 2/2007 |
| WO | WO 2007/106356 A2 | 2/2007 |
| WO | WO 2007/038988 A1 | 4/2007 |
| WO | WO 2007/050685 A2 | 5/2007 |
| WO | WO 2007/081264 A1 | 7/2007 |
| WO | WO 2007/082540 A1 | 7/2007 |
| WO | WO 2007/106431 A2 | 9/2007 |
| WO | WO 2007/111891 A2 | 10/2007 |
| WO | WO 2007/121137 A2 | 10/2007 |
| WO | WO 2008/024136 A2 | 2/2008 |
| WO | WO 2008/030999 A2 | 3/2008 |
| WO | WO 2008/039910 A2 | 4/2008 |
| WO | WO 2008/089081 A1 | 7/2008 |
| WO | WO 2008/090551 A2 | 7/2008 |
| WO | WO 2008/137353 A1 | 11/2008 |
| WO | WO 2009/010975 A1 | 1/2009 |
| WO | WO 2009/017541 A1 | 2/2009 |
| WO | WO 2009/068043 A2 | 6/2009 |
| WO | WO 2009/139878 A1 | 11/2009 |
| WO | WO 2010/006620 A1 | 1/2010 |
| WO | WO 2010/130261 A1 | 11/2010 |
| WO | WO 2011/011023 A1 | 1/2011 |
| WO | WO 2011/019359 A1 | 2/2011 |
| WO | WO 2011/026929 A1 | 3/2011 |
| WO | WO 2011/034911 A1 | 3/2011 |
| WO | WO 2011/079129 A1 | 6/2011 |
| WO | WO 2011/109393 A1 | 9/2011 |
| WO | WO 2011/147803 A1 | 12/2011 |
| WO | WO 2012/006629 A2 | 1/2012 |
| WO | WO 2012/013662 A1 | 2/2012 |
| WO | WO 2012/016179 A1 | 2/2012 |
| WO | WO 2012/016570 A2 | 2/2012 |
| WO | WO 2012/016571 A2 | 2/2012 |
| WO | WO 2012/060699 A1 | 5/2012 |
| WO | WO 2012/079590 A1 | 6/2012 |
| WO | WO 2012/085107 A2 | 6/2012 |
| WO | WO 2012/110755 A2 | 8/2012 |
| WO | WO 2012/134804 A1 | 10/2012 |
| WO | WO 2012/154946 A1 | 11/2012 |
| WO | WO 2012/156478 A1 | 11/2012 |
| WO | WO 2012/166045 A1 | 12/2012 |
| WO | WO 2012/166967 A1 | 12/2012 |
| WO | WO 2013/029620 A1 | 3/2013 |
| WO | WO 2013/029621 A1 | 3/2013 |
| WO | WO 2013/029622 A1 | 3/2013 |
| WO | WO 2013/075725 A1 | 5/2013 |
| WO | WO 2013083137 A1 | 6/2013 |
| WO | WO 2013/098190 A1 | 7/2013 |
| WO | WO 2013/105091 A1 | 7/2013 |
| WO | WO 2014/062223 A1 | 4/2014 |
| WO | WO 2014/062225 A1 | 4/2014 |
| WO | WO 2014/074141 A1 | 5/2014 |
| WO | WO 2014/074147 A1 | 5/2014 |
| WO | WO 2014081859 A1 | 5/2014 |
| WO | WO 2014/085597 A1 | 6/2014 |
| WO | WO 2014/093056 A1 | 6/2014 |
| WO | WO 2014/139767 A2 | 9/2014 |
| WO | WO 2014/140328 A1 | 9/2014 |
| WO | WO 2014/142895 A1 | 9/2014 |
| WO | WO 2014/142917 A1 | 9/2014 |
| WO | WO 2014/142923 A1 | 9/2014 |
| WO | WO 2014/142930 A1 | 9/2014 |
| WO | WO 2014/144714 A1 | 9/2014 |
| WO | WO 2014/145211 A2 | 9/2014 |
| WO | WO 2014/147620 A1 | 9/2014 |
| WO | WO 2014/149276 A1 | 9/2014 |
| WO | WO 2014/159869 A2 | 10/2014 |
| WO | WO 2014/165046 A1 | 10/2014 |
| WO | WO 2014/176486 A1 | 10/2014 |
| WO | WO 2014/176867 A1 | 11/2014 |
| WO | WO 2015/065725 A1 | 5/2015 |
| WO | WO 2015/066673 A1 | 5/2015 |
| WO | WO 2015/075841 A1 | 5/2015 |
| WO | WO 2016/044379 A2 | 3/2016 |
| WO | WO 2016/094606 A1 | 6/2016 |
| WO | WO 2017/024106 A1 | 2/2017 |
| WO | WO 2017/174715 A1 | 10/2017 |

(56) References Cited

FOREIGN PATENT DOCUMENTS

| | | |
|---|---|---|
| WO | WO 2017/185029 A1 | 10/2017 |
| WO | WO 2015/120119 A1 | 8/2018 |
| WO | WO 2015/184365 A1 | 12/2018 |

OTHER PUBLICATIONS

Urinary Incontinence Applicance, Aids, and Equipment, R/N.P. Carroll, retrieved on April 3, 2-14 from http://link.springer.com/chapter10.1007/978-1-4471-1461-1_6#, Dec. 31.

International Search Report, issued in connection with International Application No. PCT/US2014/053573 on Feb. 24, 2015.

International Search Report, issued in connection with International Application No. PCT/US2015/033344 on Mar. 12, 2015.

"Total Body Relief and Hygeine for Travel, home bath and life's less comfortable moments", http://www.biorelief.com/blog/self-cath-fits-in-your-pocket/, dated Apr. 19, 2014.

"International Search Report and Written Opinion", issued in connection with International Application No. PCT/US18/56693 on Feb. 25, 2019, 12 pages.

"International Preliminary Report on Patentability", issued in connection with International Application No. PCT/US18/56693 on Apr. 28, 2020, 7 pages.

\* cited by examiner

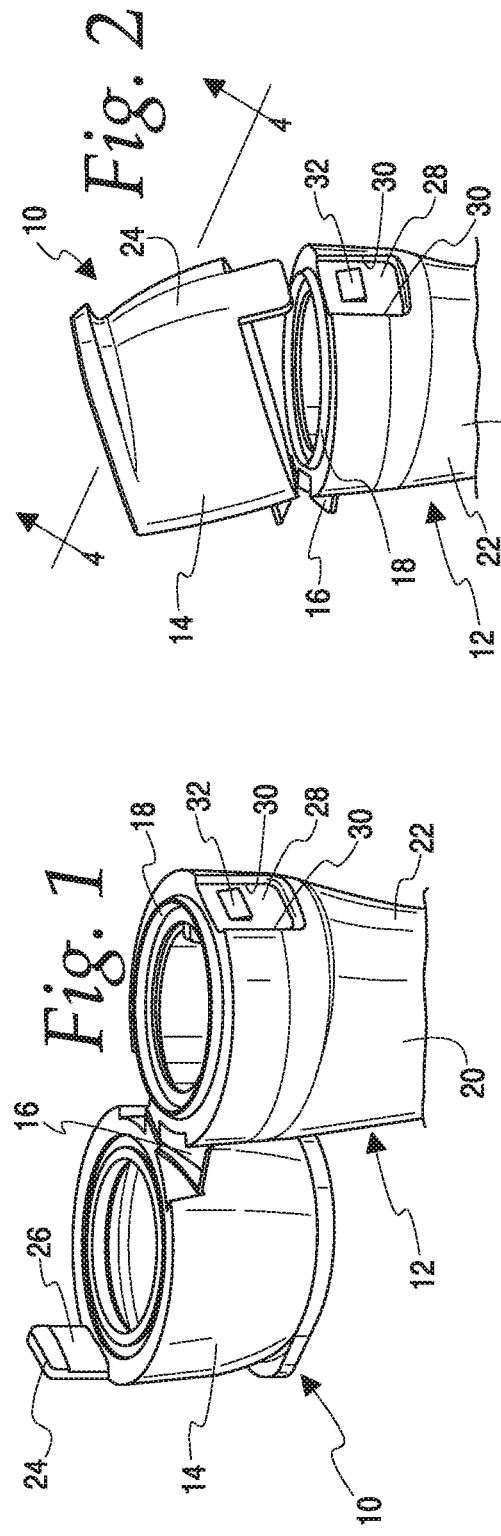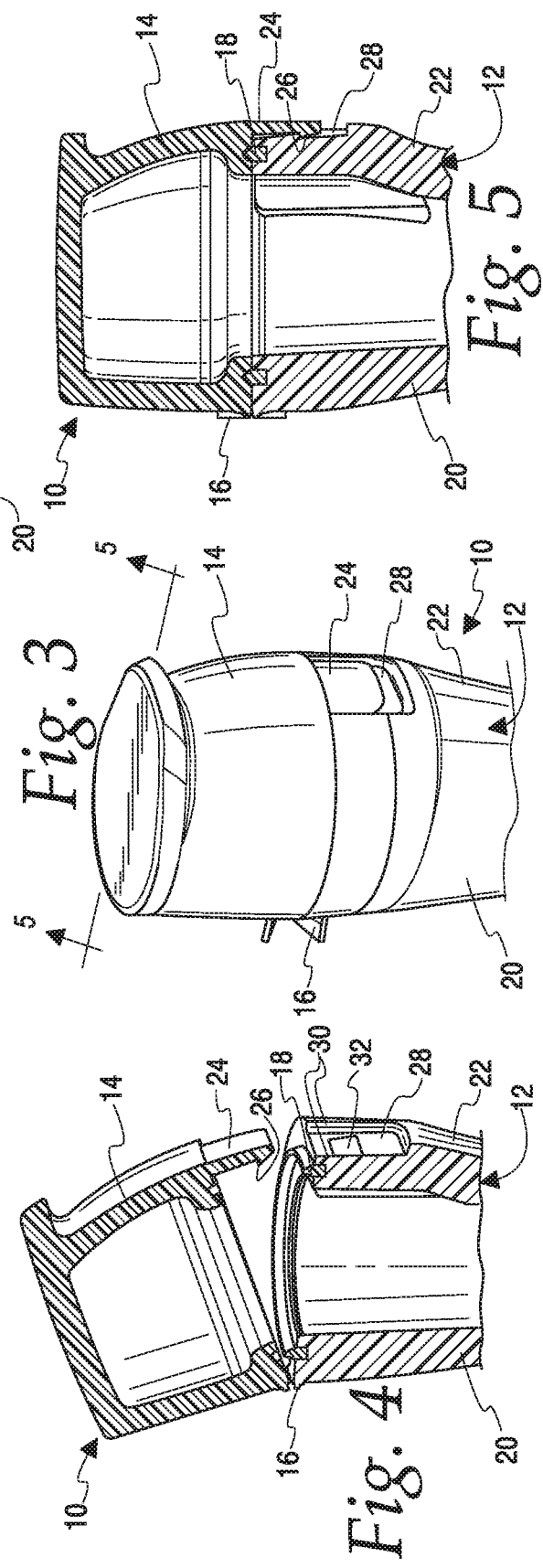

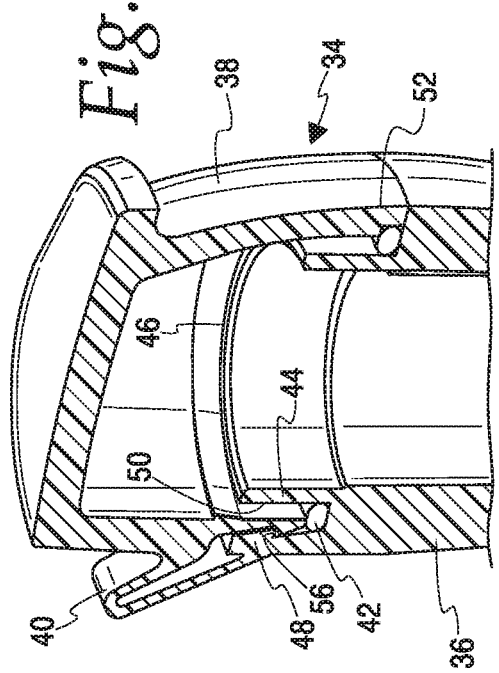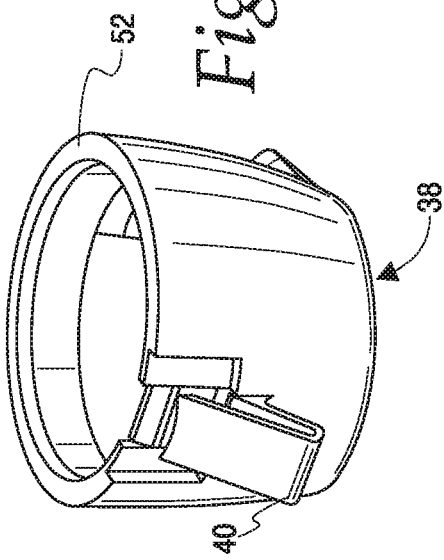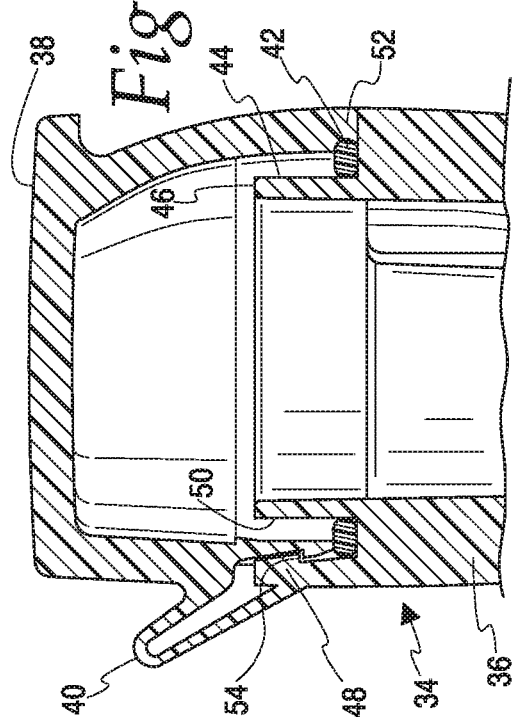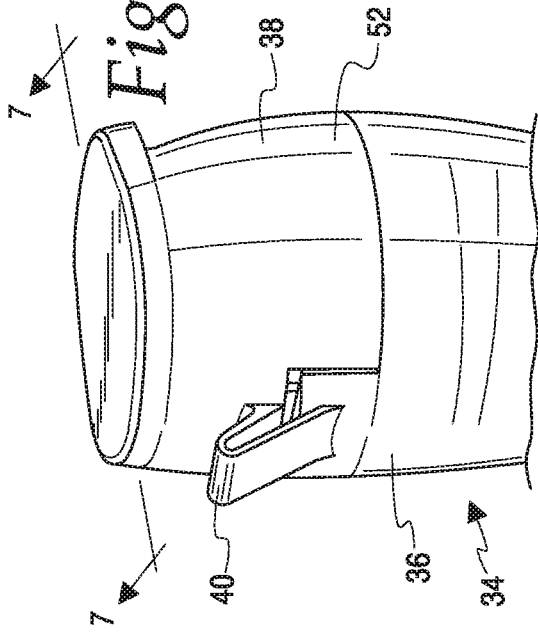

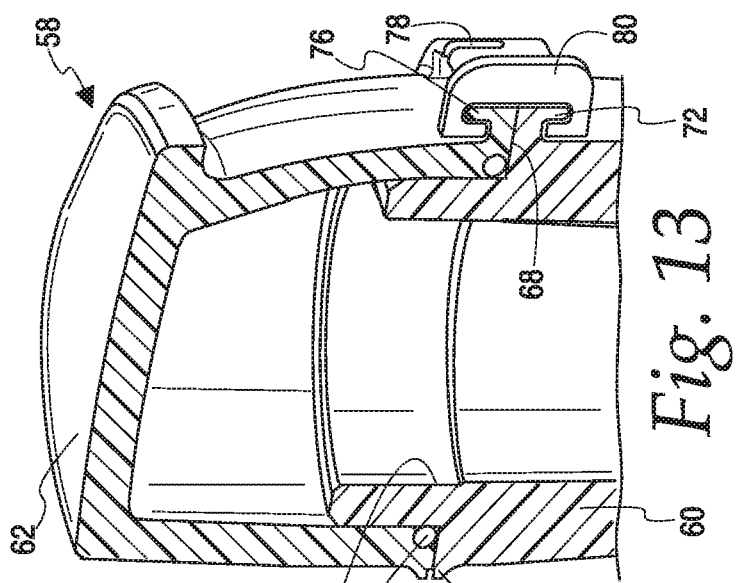
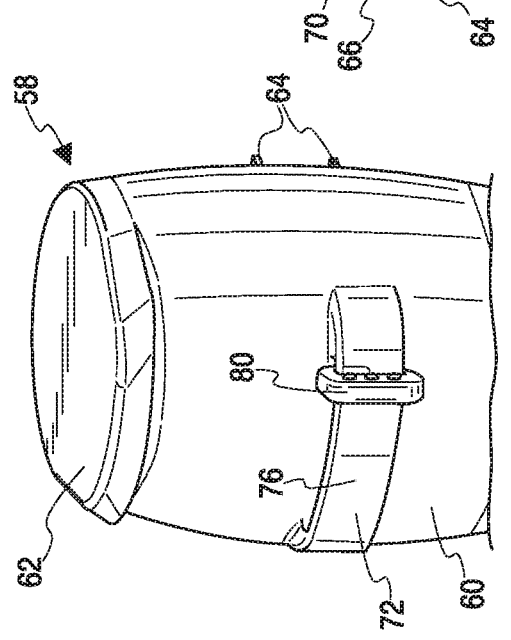
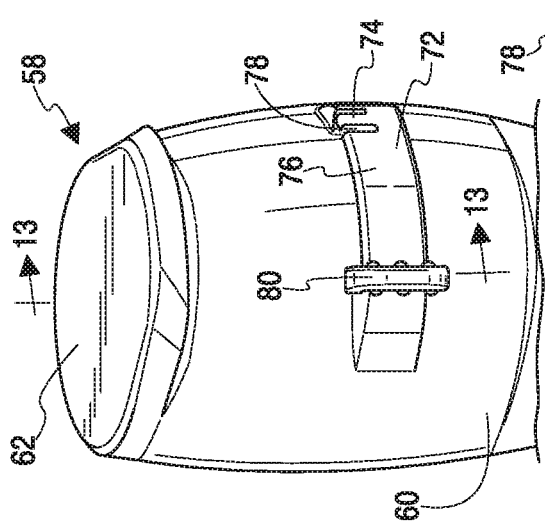
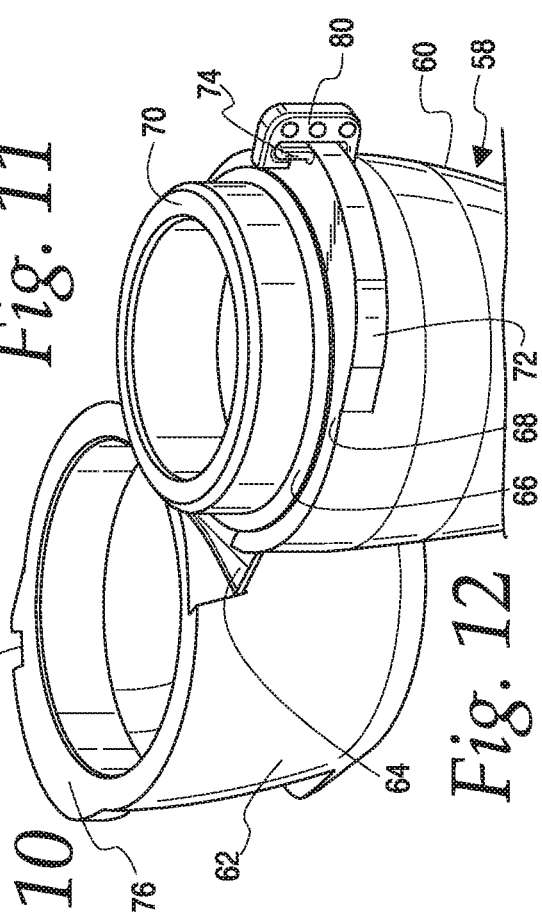
Fig. 10
Fig. 11
Fig. 12
Fig. 13

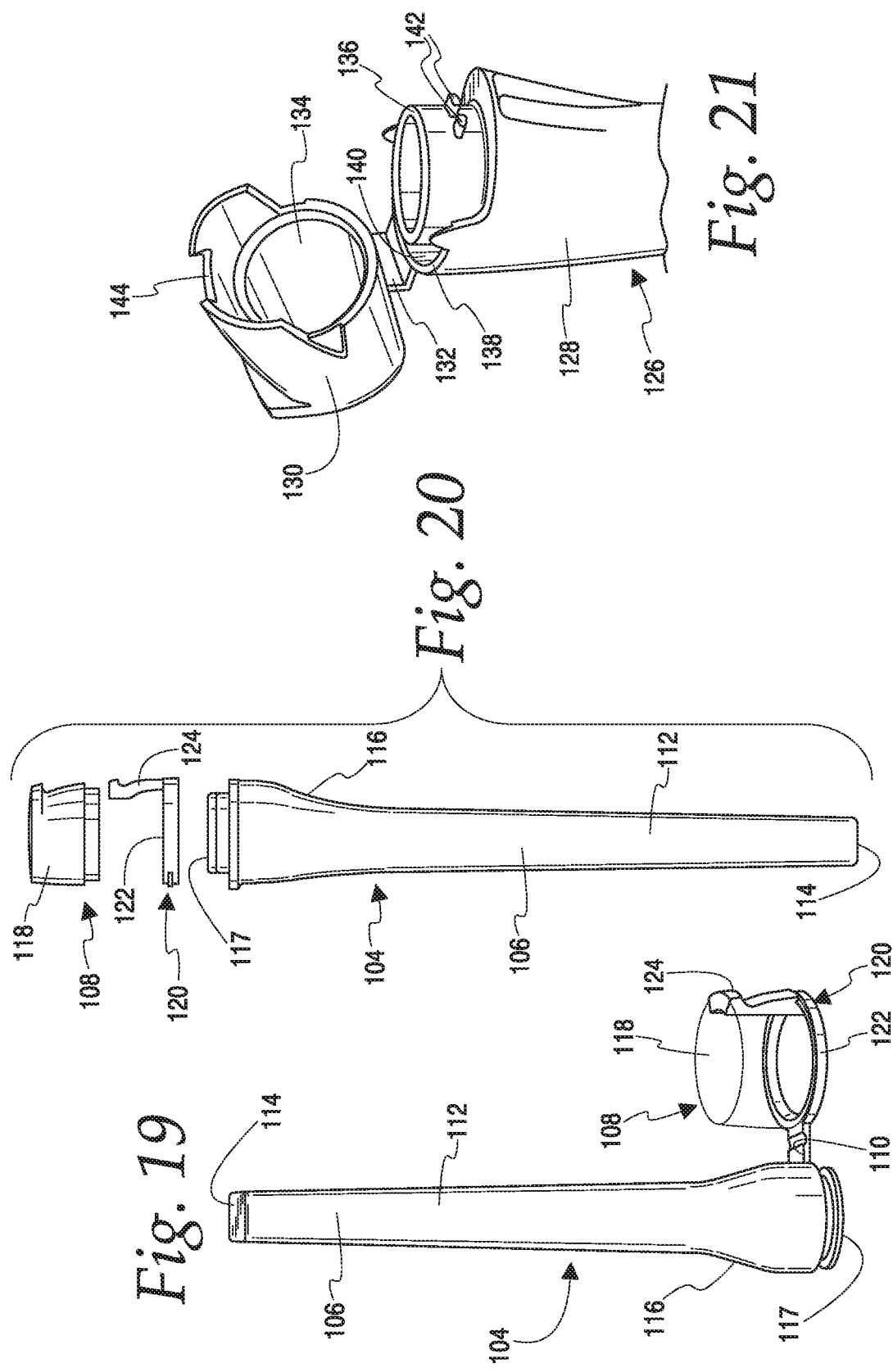

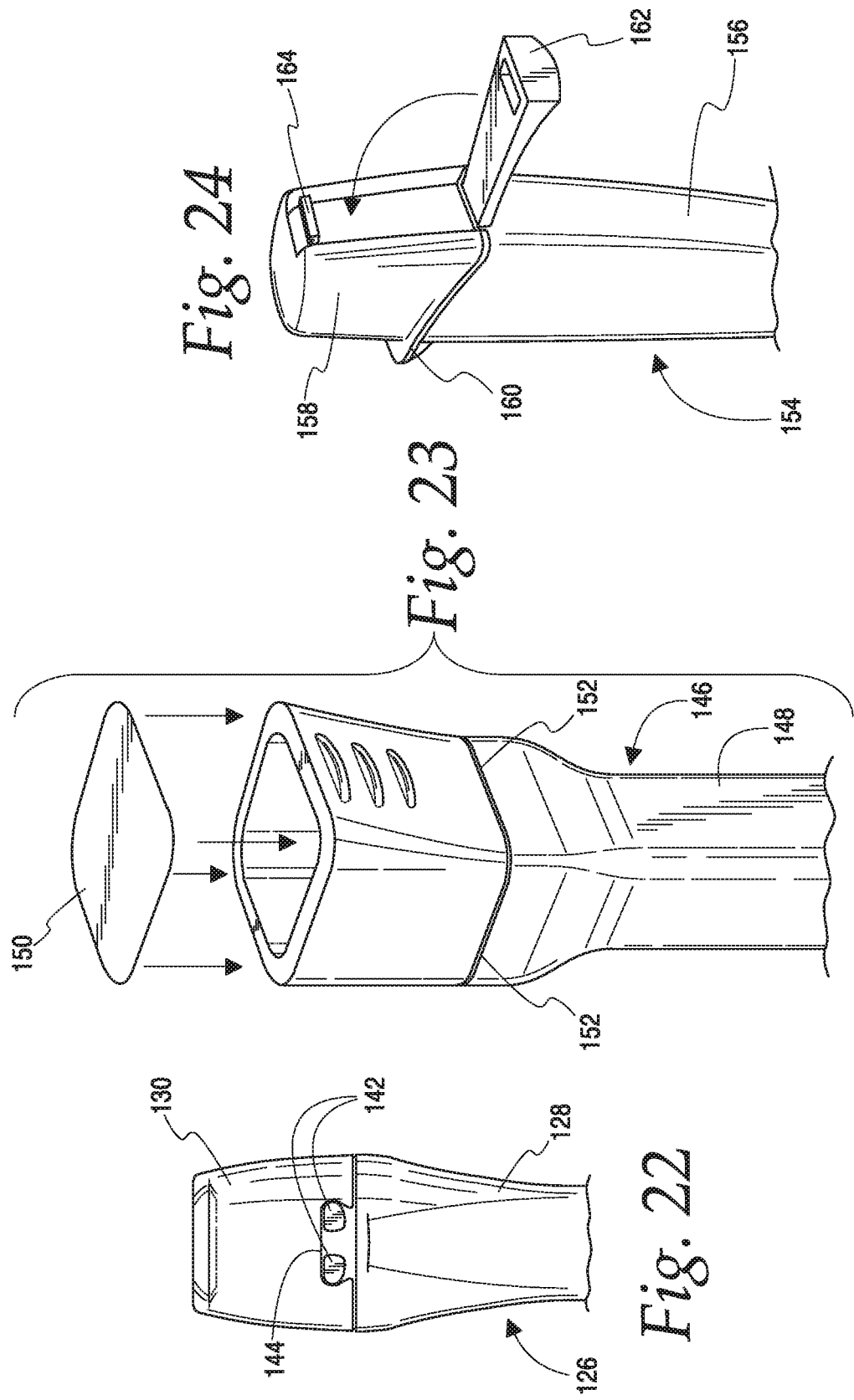

CAPS FOR CATHETER PACKAGES

CROSS-REFERENCE TO RELATED APPLICATION

The present application is a Divisional of U.S. Nonprovisional application Ser. No. 18/074,794, filed Dec. 5, 2022, which is a Divisional of U.S. Nonprovisional application Ser. No. 16/755,310, filed Apr. 10, 2020, which is a National Stage of PCT International Application No. PCT/US2018/056693 filed Oct. 19, 2018, which claims the benefit of and priority to U.S. Provisional Patent Application Ser. No. 62/577,035, filed Oct. 25, 2017, the disclosures of all of which are hereby incorporated by reference in their entireties.

FIELD OF THE DISCLOSURE

This disclosure relates generally to packaging for medical devices such as urinary catheters. More particularly, this disclosure relates to compact catheters, such as urinary catheters, and the packaging, storing and hydrating/lubricating of such catheters.

BACKGROUND

Intermittent catheterization is a good option for many users who suffer from a neurogenic bladder, that is, an atonic or unstable bladder associated with a neurological condition, such as diabetes, stroke, or spinal cord injury. Very often a neurogenic bladder is caused by conditions which may also result in diminished dexterity of the user.

Commonly, in intermittent catheterization single use, individually packaged, sterile catheters are used. Catheters often include a surface treatment that reduces friction to allow for easier and less traumatic insertion into and through the user's urethra.

Regardless of whether a surface treatment is used or what type of surface treatment is used, some type of package for the catheter is required. In the past various kinds of packages have been used, including molded containers of assorted sizes and shapes, bags and pouches made of plastic or metal foil, and similar kinds of devices While these prior art packages generally accomplish the objective of protecting the catheter during transport, storage and preparation for use, they suffer from disadvantages that range from fundamental—the packages may break open prematurely; to economic—the package designs are wasteful of material and labor; to the annoying—the packages confuse users as to how to open them or are difficult for a user of low dexterity to easily access the catheter, or the packages tend to spill the hydrating medium upon opening.

Accordingly, what is needed is a catheter package that is economical to manufacture and fill, reliable throughout its useful life, and simple and intuitive to use. It is also desirable to have a compact package which is can be discreetly carried by the user in a purse or pouch; discrete to dispose of in a waste bin; and intuitive and easy to open, particularly by a user with low dexterity. Additional desirable features of the package include easy removal of the catheter from the case; easy reclosing of the case after use; hygienic use; and it should be discreet and clean to carry after use.

Because users often carry intermittent catheters with them in containers such as purses, handbags, shoulder bags, backpacks and the like, the sealed catheter package should be capable of withstanding compression and other forces to which such containers are typically subjected. More particularly, the catheter package should remain sealed even when subjected to such forces so as to, among other things, maintain the sterility of the catheter within the package.

Furthermore, users will often prefer to return a used catheter to their purse or bag for subsequent disposal. Accordingly, the catheter package should be capable of receiving a used catheter back in the package and then being reclosed in a sealed and secured manner. Thus, a catheter package with a reliably reclosable cap would also be desired. Convenience may be further enhanced if the reclosable cap is attached to the remainder of the package so the cap does not become misplaced during use of the catheter.

As described above, many users of intermittent catheters have limited manual dexterity that can make it difficult for them to open a package and extract a catheter from the package. Thus, while reliable and secure capping and re-capping are a desired aspect of a compact catheter, also desired is the ability to easily open the package, access and extract the catheter. Accordingly, it would be desirable to provide a catheter and catheter package wherein extraction of the catheter is made easier by presenting at least a portion of the catheter (that is not inserted into the urethra of the user, such as the funnel) beyond an open end of the package when the cap is removed. Thus, the end of the funnel is presented for easy extraction and/or for easy and hygienic attachment of a urine collection bag, if desired.

Of course, having at least a portion of catheter or the funnel extending beyond the open end of the package may make the above-described sterile sealing, capping and recapping operations more difficult to achieve. For example, providing a cap hinge that is unobtrusive but affords an arc of motion for the cap that allows the cap to clear the funnel during opening and closing movements and attain the aforementioned sealing (capping) and re-sealing (e.g., "dynamic sealing") presents one challenge. Still another challenge is providing a cap that can be configured to achieve reliable sealing over an extending portion of the catheter (e.g., funnel) while withstanding the forces and loads to which it may be subjected while being carried in a handbag, purse or other receptacle which can compromise the seal. Side loads, i.e., radial or tangential loads on the cap can be a particular problem, especially on the portion of the cap opposite the hinge location. The catheter packages described herein address these concerns.

SUMMARY

In one aspect, the present disclosure is directed to a catheter package, including a case having a hollow tube which is closed at one end and open at the other end, and a cap. The package may include a hinge having one end connected to the cap and a second end connected to said other end of the hollow tube. The hinge permits selectable movement of the cap between an open position, wherein access is provided to the open end of the hollow tube, and a closed position, wherein the cap prevents access to the open end of the hollow tube. A seal is connected to at least one of the cap and case. The seal is engageable with the other of the cap and case when the cap is in the closed position to form a barrier between the cap and case that maintains a sterile environment inside the case and cap.

In another aspect, the present disclosure is directed to a catheter package including a case having a hollow tube which is closed at one end and open at the other end and a cap. The package may include a hinge having one end connected to the cap and a second end connected to the other end of the hollow tube. The hinge permits selectable movement of the cap between an open position, wherein access is provided to the open end of the hollow tube, and a closed position, wherein the cap prevents access to the open end of the hollow tube. A seal connected to at least one of the cap and case is provided. The seal is engageable with the other of the cap and case when the cap is in the closed position to form a seal between the cap and case that can be repeatedly made and broken whenever the user closes or opens the cap, respectively.

In a further aspect, the present disclosure is directed to a catheter package that has a hollow plastic case for receiving the catheter. The case has a generally tubular wall closed at one end by a bottom wall. The opposite end of the case is open and has a cap attached to it by a hinge. The cap is selectably movable between open and closed positions in which the cap uncovers or covers the open end of the case, respectively. The cap has a tab extending from the bottom edge of the cap with a hook on the bottom edge of the tab. A depression is formed on the top of the case where it can receive the tab. There is a detent in the depression. When the cap is placed in the closed position the tab fits into the depression and the hook engages the detent to retain the cap in the closed position by releasably resisting vertical lifting forces on the cap. Engagement of the tab in the depression also prevents lateral forces on the closed cap from dislodging the cap or impairing its seal.

In a still further aspect, the present disclosure is directed to a catheter package that has a hollow plastic tube for receiving the catheter. The tube has a generally cylindrical wall closed at one end by a bottom wall. The opposite end of the cylindrical wall has a cylindrical ferrule which is open at its end and defines a rim. At least partially surrounding the ferrule is a collar. At least a portion of the collar is separated from the ferrule, leaving a gap between the ferrule and the collar. The cap is attached by a hinge to the collar. The cap is selectably movable between open and closed positions in which the cap uncovers or covers the open end of the ferrule, respectively. The cap may have a skirt which surrounds the ferrule to cover the ferrule completely. A tongue on the collar is engageable with a groove on the exterior of the cap to retain the cap in the closed position when the cap is pivoted onto the top of the case.

In another aspect, the present disclosure is directed to a catheter package that has a hollow plastic tube for receiving the catheter. The tube has a wall of generally rectangular cross section and is closed at one end by a bottom wall. The opposite end of the tube's wall flares outwardly to an enlarged shoulder with a top land. A cap is attached to the tube by a hinge which allows the cap to move selectably between open and closed positons on the tube. The bottom of the cap has a sealing surface that engages the shoulder when the cap is closed. A seal is placed between the cap and shoulder to seal the interior of the package. Just below the shoulder there is an arcuate rail on the exterior of the tube. A similar rail is located on the exterior of the cap at the cap's lower edge. The cap's rail has a gap in it. A movable slider is engageable with the rails and slidable therealong to alternately lock the closed cap and tube together or unlock the cap for opening when the slider is moved so as to be opposite the gap in the cap rail. Placing the slider in the gap allows opening of the cap.

In another aspect the present disclosure is directed to a catheter package having a hollow plastic case for receiving the catheter. The case has a generally cylindrical wall closed at one end by a bottom wall. The opposite end of the cylindrical wall has a generally cylindrical ferrule which is open at its end and defines a rim. A cap is attached to the case by a hinge. The cap is made of a relatively stiff material and is engageable with the ferrule to resist side loads. The interior of the cap carries a dome-shaped bell made of a softer material than the cap itself. When the cap is closed the bell is engages the ferrule to seal the case.

In yet another aspect the present disclosure is directed to a catheter package having a hollow plastic case for receiving the catheter and a soft cap for selectably opening and closing the case. The cap has a frame made of a relatively rigid material and which includes an annular ring and an axial spine. The remainder of the cap is attached to the frame and spine and is made of a material softer than the frame.

In a still further aspect, the present disclosure is directed to a catheter package that has a hollow plastic case for receiving the catheter. One end of the case has a cylindrical ferrule which is open at its end and defines a rim. At least partially surrounding the ferrule is a collar. At least a portion of the collar is separated from the ferrule, leaving a gap between the ferrule and the collar. A cap is attached by a hinge to the collar. The cap is selectably movable between open and closed positions in which the cap uncovers or covers the open end of the ferrule, respectively. A soft liner on the interior of the cap engages the ferrule when the cap is closed to seal the ferrule. Latch fingers extend radially from the ferrule. The cap may have a skirt which has an opening for receiving the latch fingers to releasably retain the cap in a closed position.

In an additional aspect, the present disclosure is directed to a catheter package that has a hollow plastic case for receiving the catheter. The case is molded with an open top that is sealed with a separate cover. The cover can be a heat sealed foil or the like. The package can be opened by removing the cover. Alternately, the package can be opened by breaking through a molded-in, thin wall section of the case near the top.

In a further additional aspect, the present disclosure is directed to a catheter package that has a hollow plastic case for receiving the catheter. The case has a generally tubular wall closed at one end by a bottom wall. The opposite end of the case is open and has a cap attached to it by a hinge. The cap is selectably movable between open and closed positions in which the cap uncovers or covers the open end of the case, respectively. A locking arm is pivotably connected to the case. The locking arm can pivot upwardly to engage a detent on the cap when the cap is closed and thereby retain the cap in the closed position.

Most of the packages of the present disclosure permit a user to retrieve the catheter from the case and re-capture it if they so wish. Once the cap is locked back into its closed position the package retains its original sealing qualities (meaning it will not leak), with a feature, such as a label that breaks upon opening, indicating that the product has been used. Another potential indication of use could be stress marks created in the hinge when the user first opens the product.

BRIEF DESCRIPTION OF THE DRAWINGS

FIG. 1 is a perspective view of a first embodiment of the open or upper end portion of the catheter package of the present disclosure, with the cap in the fully open position.

FIG. 2 is a perspective view of the package of FIG. 1, with the cap shown in a partially open position.

FIG. 3 is a perspective view of the package of FIG. 1, with the cap in the fully closed position.

FIG. 4 is a section taken along line 4-4 of FIG. 2.

FIG. 5 is a section taken along line 5-5 of FIG. 3.

FIG. 6 is a perspective view of a second embodiment of the package of the present disclosure, with the cap in the fully closed position.

FIG. 7 is a section taken along line 7-7 of FIG. 6.

FIG. 8 is a perspective view of the section of FIG. 7.

FIG. 9 is a perspective view of the inside of the cap of the second embodiment.

FIG. 10 is a perspective view of a third embodiment of the catheter package of the present disclosure, with the cap in the fully closed position.

FIG. 11 is a perspective view of the package of FIG. 10 viewed from a different angle and with the locking slide moved to the open position.

FIG. 12 is a view similar to FIG. 10 but with the cap and locking slide in the fully open position.

FIG. 13 is a section taken along line 13-13 of FIG. 10.

FIG. 19 is a perspective view of a fifth embodiment of the catheter package of the present disclosure, with the cap in a fully open position.

FIG. 20 is an exploded side elevation view of the package of FIG. 19.

FIG. 21 is a perspective view of a sixth embodiment of the catheter package of the present disclosure, with the cap in a partially open position.

FIG. 22 is a front elevation view of the package of FIG. 21 with the cap in the closed position.

FIG. 23 is an exploded perspective view of a seventh embodiment of the catheter package of the present disclosure.

FIG. 24 is a perspective view of an eighth embodiment of the catheter package of the present disclosure.

DETAILED DESCRIPTION OF THE EMBODIMENTS

Figure 17:
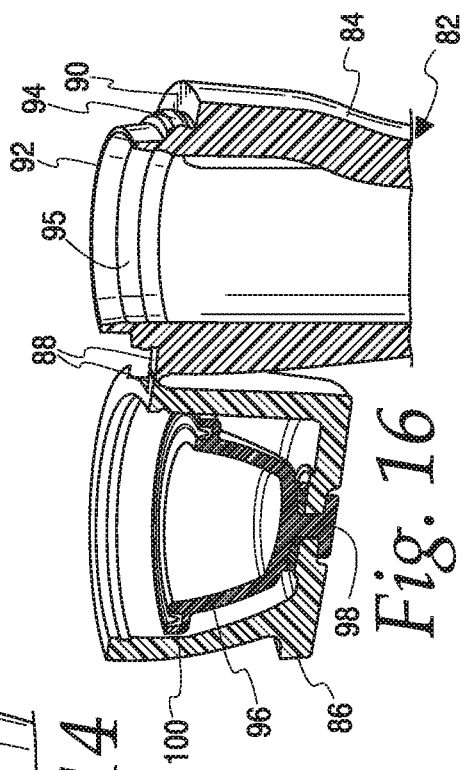
FIG. 17 is a longitudinal section of the package of FIG. 14, on an enlarged scale.

The present disclosure is directed to packages for medical devices such as intermittent urinary catheters. A first embodiment of such a package is shown generally at 10 in FIGS. 1-5. The major components of the package include a case 12, a cap 14, a hinge 16 connecting the cap 14 and case 12, and a seal ring 18. The case is preferably molded from a suitable plastic material, such as polypropylene, although other materials could be used. The case includes a hollow tubular wall 20. Only the open or upper end portion of the tubular wall is shown. The lower end is broken away. The tubular wall 20 terminates at its lower end at a transverse end wall (not shown) that closes the bottom of the tubular wall. The interior surface of the tubular wall may be generally cylindrical. The exterior surface of the tubular wall 20 may have either a cylindrical or rectangular cross-sectional shape or the cross-section could be otherwise. The upper end portion of the tubular wall 20 flares outwardly somewhat at a neck portion 22 to increase the diameter of the tube. The top of the neck 22 terminates at an open end of the tubular wall 20.

The hinge 16 as shown is a living hinge, but other hinge arrangements could be used. The hinge connects to the case 12 and the cap 14 to permit selectable movement of the cap between open and closed positions. The cap 14 is selectably movable between the open position shown in FIGS. 1, 2 and 4 and the closed position shown in FIGS. 3 and 5. The cap uncovers or covers the open end of the case in the open and closed positions, respectively.

The cap has a tab 24 extending from the bottom edge of the cap. There is an inwardly directed hook 26 on the bottom edge of the tab 24. A depression 28 is formed on the top of the case 12 and defines side edges 30. The depression is aligned with the tab 24 when the cap is closed. There is a detent 32 formed in the depression 28. When the cap is placed in the closed position the tab 24 fits into the depression 28 as seen in FIGS. 3 and 5. The tab flexes to allow the hook 26 to slide past the detent 32 and engage the detent to retain the cap 14 in the closed position by releasably resisting vertical lifting forces on the cap. Since the closed tab 24 is also immediately adjacent the sides edges 32 defined by the depression 28, the tab also prevents lateral forces on the closed cap from dislodging the cap or impairing its seal. The seal is formed when the cap is closed by engagement of the bottom land of the cap with the upwardly protruding portion of the seal ring 18. This seal is dynamic in that it can be made and released multiple times as the cap is closed or opened.

A second embodiment of a package for medical devices such as intermittent urinary catheters is shown generally at 34 in FIGS. 6-9. The major components of the package once again include a case 36, a cap 38, a hinge 40 connecting the cap 38 and case 36, and a seal ring 42. As in the previous embodiment, the case 36 is a generally hollow plastic tube for receiving the catheter. The tube has a generally cylindrical wall closed at one end by a bottom wall (not shown). The opposite end of the cylindrical wall has a cylindrical ferrule 44 which is open at its end and defines a rim 46. At least partially surrounding the ferrule is a collar 48. At least a portion of the collar 48 (on the left side of FIGS. 7 and 8) is separated from the ferrule 44, leaving a gap 50 between the ferrule 44 and the collar 48. The cap 38 is attached by the U-shaped hinge 40 to the collar 48. The cap is selectably movable between open and closed positions in which the cap 38 uncovers or covers the open end of the ferrule 44, respectively. The cap may have a skirt 52 which surrounds the ferrule 44 to cover it completely when the cap is closed. Also, when the cap is closed a portion of the skirt 52 fits within the gap 50 and the skirt 52 engages the seal ring 42. A tongue 54 on the interior of the collar 48 is engageable with a groove 56 on the exterior of the cap's skirt 52 to retain the cap 38 in the closed position when the cap is pivoted onto the top of the case.

A third embodiment of a package for urinary catheters is shown generally at 58 in FIGS. 10-13. As in the previous embodiments the major components of the package include a case 60, a cap 62, a hinge 64 connecting the cap 62 and case 60, and a seal ring 66. The case 60 once again is a tube with a cylindrical wall closed at one end by a bottom wall (not shown). The opposite end of the tube's wall has a radial shoulder 68 with a ferrule 70 extending axially above the shoulder. The seal ring 66 rests on top of the shoulder 68. The bottom of the cap 62 has a sealing surface that engages the shoulder 68 and the seal ring 66 when the cap is closed. Just below the shoulder 68 there is an arcuate rail 72 on the exterior of the case. There is a retaining post 74 that extends above the shoulder 68 but is attached to the shoulder. Another rail 76 is located on the exterior of the cap at the cap's lower edge. The cap's rail 76 has a gap 78 in it that receives the retaining post 74 when the cap is closed. A movable, C-shaped locking slide 80 has hooks or fingers that are engageable with the rails 72 and 74. The locking slide is arcuately movable along the rails to alternately lock the closed cap and tube together or unlock the cap for opening. The locking slide is always engaged with the case rail 72. It is alternately engaged with either the cap rail 74 or the retaining post 74. When the slide 80 is moved so as to be opposite the gap 78 in the cap rail 76 the slide engages the retaining post 74 and releases the cap. Placing the slide opposite the gap 76 disengages the slide from the cap rail 74 to permit opening of the cap. Reclosing the cap places the gap 78 around the slide 80 and allows the slide to be moved laterally back into engagement with the cap rail 76, thereby locking the cap to the case.

Figure 16:
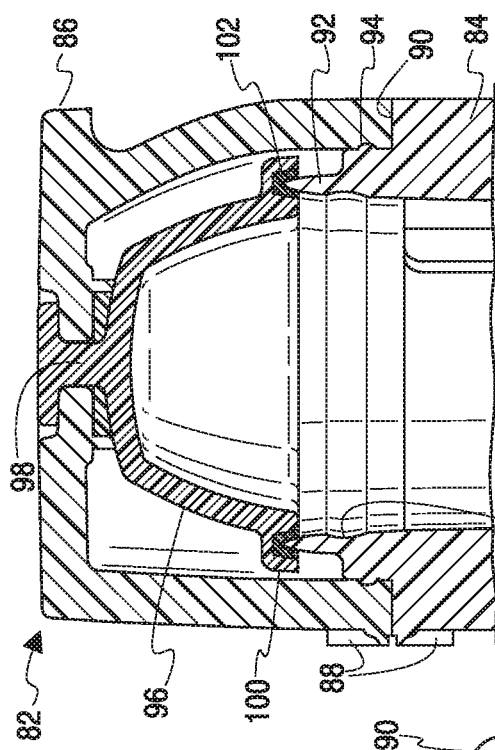
FIG. 16 is a section taken along line 16-16 of FIG. 15.
Figure 14:
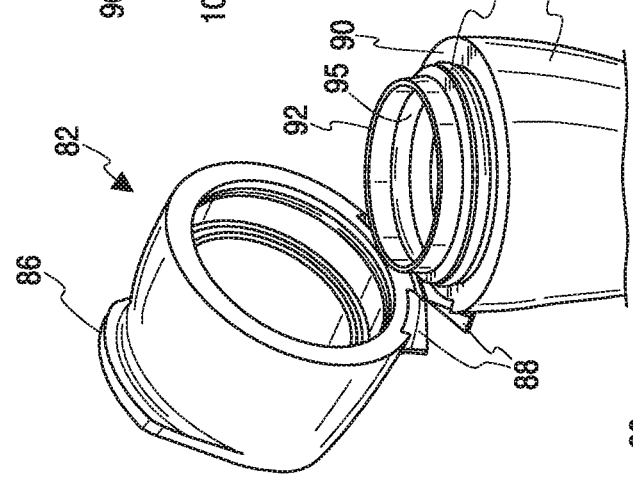
FIG. 14 is a perspective view of a fourth embodiment of the catheter package of the present disclosure, with the cap in the partially open position.
Figure 18:
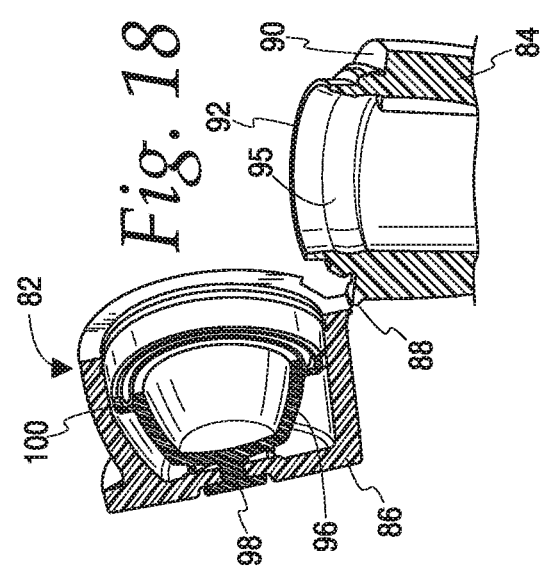
FIG. 18 is a section, similar to FIG. 16 but showing the cap partially open.
Figure 15:
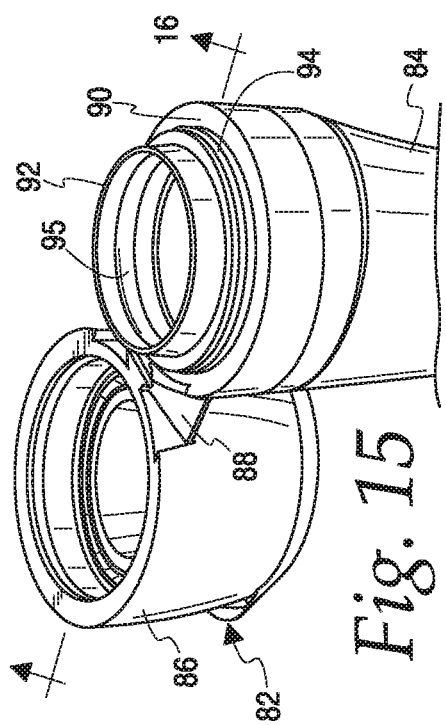
FIG. 15 is a view similar to FIG. 14 but with the cap fully open.

A fourth embodiment of a package for urinary catheters is shown generally at 82 in FIGS. 14-18. As in the previous embodiments the major components of the package include a case 84, a cap 86, and a hinge 88 connecting the cap 86 and case 84. The case has a generally cylindrical wall closed at one end by a bottom wall (not shown). The opposite end of the cylindrical wall has a radial shoulder 90 with a ferrule 92 extending axially above the shoulder. There is an enlargement at the junction of the shoulder and ferrule. An outwardly-protruding, radial bead 94 is formed on the enlargement. The bead is engageable with a groove in the interior of the cap when the cap is closed. The bead and cap are made of relatively stiff materials so as to resist side loads on the cap. The interior of the cap carries a dome-shaped bell 96 made of a softer material than the cap itself. The bell is connected to the cap by a post 98. The lower edge of the bell has a flange sized to engage the top of the ferrule 92 when the cap is closed to seal the case. The soft material of the bell affords a tight seal on the harder ferrule. Alternately, a seal ring 102 could be carried on the underside of the flange 100.

A fifth embodiment of a package for urinary catheters is shown generally at 104 in FIGS. 19-20. This package includes a case 106, a cap 108, and a hinge 110 connecting the cap 108 to the case 106. The case includes a hollow tubular wall 112. The tubular wall 112 terminates at its lower end at a transverse end wall 114 that closes the bottom of the tubular wall. The upper end portion of the tubular wall 112 flares outwardly somewhat at a neck portion 116 to increase the diameter of the tube. The top of the neck 116 terminates at an open end 117 of the tubular wall 112. The hinge 110 permits selectable movement of the cap 108 between open and closed positions. The cap has a soft shell 118 supported by a frame 120 made of a relatively rigid material. The frame has an annular ring 122 and an axial spine 124. The soft shell 118 of the cap 108 is attached to the annular ring 122 and the spine 124 and is made of a material that is softer than these parts of the frame 120.

A sixth embodiment of a package for urinary catheters is shown generally at 126 in FIGS. 21-22. The package has a case 128, a cap 130, a hinge 132 connecting the cap 130 and case 128, and a seal liner 134 in the interior of the cap. The case 128 is a generally hollow tube having a wall closed at one end by a bottom wall (not shown). The opposite end of the cylindrical wall is similar to that of FIGS. 6-9 in that it has a cylindrical ferrule 136 which is open at its end. At least partially surrounding the ferrule 136 is a collar 138. At least a portion of the collar 138 is separated from the ferrule 136, leaving a gap 140 between the ferrule 136 and the collar 138. The cap 130 is attached by the hinge 132 to the collar 138. The cap is selectably movable between open and closed positions in which the cap 130 uncovers or covers the open end of the ferrule 136, respectively. The soft liner 134 on the interior of the cap 130 engages the ferrule 136 when the cap is closed to seal the ferrule. Latch fingers 142 extend radially from the ferrule 136. The cap 130 may have a skirt which has an opening 144 for receiving the latch fingers 142 to releasably retain the cap in a closed position.

A seventh embodiment of a package for urinary catheters is shown generally at 146 in FIG. 23. Package 146 includes a case 148 with an open top that is sealed with a separate cover 150. The cover can be a foil layer or the like that is heat sealed or fixed to the case 148 by an adhesive. Toward the top end of the case there is a thin-walled portion 152 on at least three sides of the case. The thin-walled portion 152 has a reduced wall thickness compared to the rest of the case. This affords a weakened connection that allows the package to be opened by breaking through the molded-in, thin-walled section 152 of the case. Alternately, the package 146 can be opened by removing or piercing the cover 150.

An eighth embodiment of a package for urinary catheters is shown generally at 154 in FIG. 24. The package has a case 156, a cap 158, a hinge 160 connecting the cap 158 and case 156. The case has a generally tubular wall closed at one end by a bottom wall. The opposite end of the case is open and has the cap attached to it by the hinge 160. The cap 158 is selectably movable between open and closed positions in which the cap uncovers or covers the open end of the case, respectively. A locking arm 162 is pivotably connected to the case 156. The locking arm 162 can pivot upwardly to engage a detent 164 on the cap 158 when the cap is closed and thereby retain the cap in the closed position.

It should be understood that various changes and modifications to the presently preferred embodiments described herein will be apparent to those skilled in the art. Such changes and modification can be made without departing from the spirit and scope of the invention disclosed herein.

The invention claimed is:

1. A urinary catheter package, comprising:
   a case having a hollow tube which is closed at one end and open at the other end, the hollow tube having a wall of unitary construction with an outer surface, wherein the wall has a thinned wall portion of reduced thickness in the outer surface of the wall; and
   a pierceable cover attached to the open end of the hollow tube.

2. The urinary catheter package of claim 1, wherein the pierceable cover is a foil layer.

3. The urinary catheter package of claim 1, wherein the pierceable cover is heat sealed to the case.

4. The urinary catheter package of claim 1, wherein the pierceable cover is fixed to the case by adhesive.

5. The urinary catheter package of claim 1, wherein the thin-walled section is on at least three sides of the case.

6. The urinary catheter package of claim 1, wherein the walls of the thin-walled section are thinner than the walls of the remaining portion of the case.

7. The urinary catheter package of claim 1, wherein the pierceable cover is a different material than the material of the case.

8. The urinary catheter package of claim 1, wherein an upper end portion of the tube wall of the case flares outwardly at a neck portion to increase the diameter of the tube.

9. The urinary catheter package of claim 1, wherein an upper end portion of the tube wall of the case flares outwardly at a neck portion to increase the diameter of the tube and includes the thin-walled section.

10. The urinary catheter package of claim 1, wherein the case is comprised of a plastic material.

11. The urinary catheter package of claim 1, wherein an upper end portion of the case has a rectangular cross-sectional shape.

12. The urinary catheter package of claim 1, wherein the thin-walled section has a rectangular cross-sectional shape.

13. The urinary catheter package of claim 1, wherein the thinned walled portion of reduced thickness is a continuous groove in the entire circumference outer surface of the wall of the hollow tube.

14. A urinary catheter assembly comprising:
   a urinary catheter package, including:
      a case having a hollow tube which is closed at one end and open at the other end, the hollow tube having a wall of unitary construction with an outer surface, wherein the wall has a thinned wall portion of reduced thickness in the outer surface of the wall; and
      a pierceable cover attached to the open end of the hollow tube; and
   a urinary catheter which includes a funnel at a first end.

15. The urinary catheter assembly of claim 14, wherein the pierceable cover is a foil layer.

16. The urinary catheter assembly of claim 14, wherein the pierceable cover is heat sealed to the case.

17. The urinary catheter assembly of claim 14, wherein the pierceable cover is fixed to the case by adhesive.

18. The urinary catheter assembly of claim 14, wherein the thin-walled section is on at least three sides of the case.

19. The urinary catheter assembly of claim 14, wherein the walls of the thin-walled section are thinner than the walls of the remaining portion of the case.

20. The urinary catheter assembly of claim 14, wherein the thinned walled portion of reduced thickness is a continuous groove in the entire circumference outer surface of the wall of the hollow tube.

* * * * *